(12) United States Patent
Mueckter et al.

(10) Patent No.: US 9,782,206 B2
(45) Date of Patent: Oct. 10, 2017

(54) IMPLANT SYSTEM FOR BONE FIXATION

(75) Inventors: Helmut Mueckter, Aachen (DE); Ingo Stoltenberg, Probsteierhagen (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 118 days.

(21) Appl. No.: 13/983,835

(22) PCT Filed: Feb. 8, 2011

(86) PCT No.: PCT/EP2011/000585
§ 371 (c)(1),
(2), (4) Date: Nov. 15, 2013

(87) PCT Pub. No.: WO2012/107056
PCT Pub. Date: Aug. 16, 2012

(65) Prior Publication Data
US 2014/0088595 A1    Mar. 27, 2014

(51) Int. Cl.
*A61B 17/56* (2006.01)
*A61B 17/72* (2006.01)
*A61B 17/74* (2006.01)

(52) U.S. Cl.
CPC ........ *A61B 17/725* (2013.01); *A61B 17/7233* (2013.01); *A61B 17/744* (2013.01)

(58) Field of Classification Search
CPC ... A61B 17/72; A61B 17/1725; A61B 17/725; A61B 17/68
(Continued)

(56) References Cited

U.S. PATENT DOCUMENTS

| 3,433,220 A | 3/1969 | Zickel |
| 4,776,330 A | 10/1988 | Chapman et al. |

(Continued)

FOREIGN PATENT DOCUMENTS

| EP | 0838199 A1 | 4/1998 |
| EP | 1175872 A2 | 1/2002 |

(Continued)

OTHER PUBLICATIONS

Gamma3 Long Nail R2, Copyright date 2004, pp. 1-52.
(Continued)

*Primary Examiner* — Jacqueline Johanas
*Assistant Examiner* — Tessa Matthews
(74) *Attorney, Agent, or Firm* — Lerner, David, Littenberg, Krumholz & Mentlik, LLP

(57) ABSTRACT

An implant system for use in orthopedic surgery for fixation of bone includes an intramedullary nail and a coupling unit. The intramedullary nail has a proximal portion defining a longitudinal axis and a transverse bore. The proximal portion includes a bore defining a first axis and a guiding structure defining a second axis, wherein the first axis and the second axis are substantially parallel to the longitudinal axis of the proximal portion of the intramedullary nail and are spaced apart from each other. The coupling unit is movably arranged within the proximal portion and includes a substantially cylindrical pin and a drive member with a through hole. The guiding structure is configured to slidably receive the substantially cylindrical pin, such that the pin can engage within a groove of a bone fastener configured to penetrate the transverse bore of the intramedullary nail.

43 Claims, 5 Drawing Sheets

(58) Field of Classification Search
USPC .................................................. 606/62–64
See application file for complete search history.

(56) References Cited

U.S. PATENT DOCUMENTS

| | | | |
|---|---|---|---|
| 5,032,125 | A | 7/1991 | Durham et al. |
| 5,176,681 | A | 1/1993 | Lawes et al. |
| 6,221,074 | B1 | 4/2001 | Cole et al. |
| 6,296,645 | B1 | 10/2001 | Hover et al. |
| 6,402,753 | B1 | 6/2002 | Cole et al. |
| 6,406,477 | B1 | 6/2002 | Fujiwara |
| 6,648,889 | B2 | 11/2003 | Bramlet et al. |
| 6,835,197 | B2 | 12/2004 | Roth et al. |
| 6,855,146 | B2 | 2/2005 | Frigg et al. |
| 6,921,400 | B2 | 7/2005 | Sohngen |
| 6,926,719 | B2 | 8/2005 | Sohngen et al. |
| 7,018,380 | B2 | 3/2006 | Cole |
| 7,041,104 | B1 | 5/2006 | Cole et al. |
| 7,182,765 | B2 | 2/2007 | Roth et al. |
| 7,306,600 | B2 | 12/2007 | Roth et al. |
| 7,591,819 | B2 | 9/2009 | Zander et al. |
| 7,763,023 | B2 | 7/2010 | Gotfried |
| 7,867,231 | B2 | 1/2011 | Cole |
| 8,092,454 | B2 | 1/2012 | Sohngen |
| 8,100,911 | B2 | 1/2012 | Yamazaki et al. |
| 8,157,801 | B2 | 4/2012 | Doubler et al. |
| 8,157,802 | B2 | 4/2012 | Elghazaly et al. |
| 8,172,841 | B2 | 5/2012 | Defossez |
| 8,303,590 | B2 | 11/2012 | Elghazaly et al. |
| 8,808,293 | B2 | 8/2014 | Buettler et al. |
| 8,840,675 | B2 | 9/2014 | Song |
| 2002/0032445 | A1 | 3/2002 | Fujiwara |
| 2002/0107578 | A1 | 8/2002 | Speitling et al. |
| 2002/0156473 | A1 | 10/2002 | Bramlet et al. |
| 2005/0069397 | A1 | 3/2005 | Shavit et al. |
| 2005/0143739 | A1* | 6/2005 | Shinjo ............... A61B 17/744 606/62 |
| 2005/0203510 | A1 | 9/2005 | Sohngen |
| 2006/0156473 | A1 | 7/2006 | Chambers et al. |
| 2006/0200160 | A1* | 9/2006 | Border et al. .................. 606/88 |
| 2007/0049938 | A1 | 3/2007 | Wallace et al. |
| 2007/0233100 | A1 | 10/2007 | Metzinger |
| 2008/0140077 | A1 | 6/2008 | Kebaish |
| 2008/0294164 | A1 | 11/2008 | Frank et al. |
| 2008/0294203 | A1 | 11/2008 | Kovach et al. |
| 2009/0048600 | A1 | 2/2009 | Matityahu et al. |
| 2010/0249781 | A1* | 9/2010 | Haidukewych et al. ....... 606/62 |
| 2010/0249852 | A1 | 9/2010 | Brumfield et al. |
| 2011/0054474 | A1* | 3/2011 | Metzinger et al. ............. 606/64 |
| 2011/0196372 | A1* | 8/2011 | Murase .......................... 606/64 |
| 2012/0197255 | A1 | 8/2012 | Elghazaly |
| 2012/0253410 | A1 | 10/2012 | Taylor et al. |
| 2013/0041414 | A1 | 2/2013 | Epperly et al. |
| 2013/0158601 | A1 | 6/2013 | Stone et al. |
| 2014/0012259 | A1* | 1/2014 | Matityahu et al. ............. 606/62 |
| 2014/0058392 | A1 | 2/2014 | Mueckter et al. |
| 2014/0088595 | A1 | 3/2014 | Mueckter et al. |
| 2014/0094802 | A1* | 4/2014 | Simon et al. ................... 606/64 |
| 2014/0330174 | A1* | 11/2014 | Warlick et al. .................. 601/2 |

FOREIGN PATENT DOCUMENTS

| | | |
|---|---|---|
| EP | 1547534 A2 | 6/2005 |
| JP | H02-21859 A | 1/1990 |
| JP | 2005205201 A | 8/2005 |
| JP | 2009148318 A | 7/2009 |
| KR | 100953149 B1 | 4/2010 |
| WO | 02098330 A2 | 12/2002 |
| WO | 03032852 A2 | 4/2003 |
| WO | 03094763 A1 | 11/2003 |
| WO | 2012107056 A1 | 8/2012 |

OTHER PUBLICATIONS

Heineman, et al., "Intra-abdominal Migration of a Lag Screw in Gamma Nailing: Report of a Case", J Orthop Trauma, Dec. 2010, vol. 24, No. 12, pp. e119-e122.

Horas, et al., "Mediate Schenkelhalsschraubendislokation nach Gammanagelosteosynthese einer pertrochantaren Femurmetastase", 2008, p. 746-748 (English translation of Abstract provided).

Li, et al., "Medical pelvic migration of the lag screw in a short gamma nail after hip fracture fixation: a case report and review of the literature", Journal of Orthopaedic Surgery and Research, 2010, 5:62, pp. 1-7.

Synthes, "Titanium Trochanteric Fixation Nail System-Screw Option. For intramedullary fixation of proximal femur fractures.", Copyright date 2010, pp. 1-67.

International Search Report for Application No. PCT/EP2011/000585 dated Jun. 27, 2011.

International Search Report for Application No. PCT/EP2012/000577 dated May 31, 2012.

Japanese Office Action for Application No. 2013-552885 dated Aug. 25, 2015.

European Examination Report for Application No. 12705227.2 dated May 5, 2015.

* cited by examiner

IMPLANT SYSTEM FOR BONE FIXATION

CROSS-REFERENCE TO RELATED APPLICATION

The present application is a national phase entry under U.S.C. §371 of International Application No. PCT/EP2011/000585 filed Feb. 8, 2011, published in English, incorporated herein by reference.

BACKGROUND OF THE INVENTION

The present disclosure generally relates to an implant system for use in orthopaedic surgery. Specifically, the disclosure relates to an intramedullary nail for internal fixation of bone, such as a femur.

Femur fractures commonly occur in the femoral neck and the trochanteric regions. Typically, trochanteric and subtrochanteric femur fractures are currently treated with an intramedullary nail having a transverse bore to receive a bone fastener, such as a femoral neck screw usually provided in the form of a lag screw. The intramedullary nail is fitted in the intramedullary canal of the femur and the lag screw passes through the transverse bore of the intramedullary nail, through the neck of the femur and into the femoral head.

The lag screw is designed to transfer the load of the femoral head into the nail shaft by bridging the fracture line to allow fast and secure fracture healing. Further, the lag screw is allowed to slide in the intramedullary nail in accordance with the sintering of the femoral fracture. Typically, a set screw is inserted into a bore of the intramedullary nail to prevent a rotation and an uncontrolled medial deviation of the lag screw.

The intramedullary nail may include a central cannulation along its longitudinal axis for receiving a surgical wire (guide wire), such as a Kirschner-wire. The surgical wire is inserted into the marrow cavity of the femur prior to the insertion of the intramedullary nail.

For example, U.S. Pat. No. 5,176,681 A relates to an intramedullary intertrochanteric fracture fixation appliance and fitting device. The intramedullary fracture fixation appliance comprises an intramedullary nail having a transverse bore for receiving a femoral neck screw in the form of a lag screw. The proximal end of the intramedullary nail is provided with another bore extending co-axially through the nail and opening into the transverse bore. A set screw is located within the co-axial bore of the nail. The lower end of the set screw has a centrally arranged protrusion. When the set screw is in its final position, the central protrusion of the set screw engages in one of longitudinally extending grooves arranged on the shaft of the lag screw.

U.S. Pat. No. 6,835,197 B2 relates to an intramedullary nail with a coupling mechanism. The coupling mechanism includes a body member and a flat prong laterally extending from the body member. Further, a short bolt for threadable engagement with a partially threaded channel that extends axially in the intramedullary nail is rotatably coupled to the body member. The body member further includes tabs, which are received in grooves of the channel, such that cooperation between the tabs and the grooves prevents rotation of the body member within the channel. When the body member is urged toward a lag screw inserted through a transverse bore of the intramedullary nail, the flat prong contacts a side surface of the lag screw and fills a void defined by the flat portion of the lag screw, such that the prong fits tightly in the space between the channel wall and the lag screw.

U.S. Pat. No. 6,648,889 B2 relates to an intramedullary nail with a bifurcated lock. Similar to the body member described in U.S. Pat. No. 6,835,197 B2, a sleeve lock includes two lateral locking tabs in the form of flat prongs and an anti-rotation tab engaging within a groove of a channel of the intramedullary nail. The locking tabs of the sleeve lock engage within locking slots of a sleeve which is arranged on the lag screw.

U.S. Pat. No. 6,406,477 B1 relates to an intramedullary nail having a set hole in its proximal portion. The proximal portion of the nail further has two transverse bores in which a lag screw and an auxiliary connector are to be located. Since the auxiliary connector extends through the nail at a location between a set screw screwed into the set hole of the intramedullary nail and the lag screw, a spacer for transmitting a clamping force is interposed between the set screw and the lag screw. The spacer includes a body and two apart legs laterally extending from the body. When the set screw is placed on the spacer in the set hole and is screwed into the set hole, the set screw pushes the entire spacer down and the lower ends of the legs engage within grooves of the lag screw. The auxiliary connector is positioned between the two legs of the spacer and is securely held by a central boss formed at the forward end of the set screw and inserted through an opening formed in the body of the spacer.

The conventional intramedullary nails have several drawbacks. A set screw without a through hole cannot be preassembled with the intramedullary nail and thus has to be inserted into the intramedullary nail intraoperatively after removal of a guide wire. In this case, the insertion of the relatively small set screw into the shaft of the intramedullary nail is cumbersome. Soft tissue overlapping the opening at the proximal end of the nail may hinder the insertion of the set screw and the mutual engagement of the threads. Thus, the set screw may get stuck within the intramedullary nail and the operation time increases due to additional operation steps. Moreover, a set screw having one or more prongs cannot prevent an uncontrolled medial deviation of the lag screw. Additionally, using set screws with prongs requires a modification of the current lag screw shaft design providing longitudinal extending grooves in which a pin of the set screw can engage to guarantee a defined sliding of the lag screw within the intramedullary nail.

BRIEF SUMMARY OF THE INVENTION

Aspects of the present disclosure are directed to providing an implant system simplifying and facilitating the surgical procedure and implantation of an intramedullary nail and corresponding bone fasteners.

According to a first aspect, there is provided an implant system for use in orthopaedic surgery for fixation of bone. The implant system comprises an intramedullary nail with a proximal portion defining a longitudinal axis, a distal portion and a transverse bore. The proximal portion includes a bore defining a first axis and a guiding structure defining a second axis. The first axis and the second axis are substantially parallel to the longitudinal axis of the proximal portion of the intramedullary nail and are spaced apart from each other. Further, the implant system comprises a coupling unit adapted to be movably arranged within the proximal portion of the intramedullary nail. The coupling unit includes a substantially cylindrical pin and a drive member with a through hole, wherein the guiding structure is configured to slidably receive the substantially cylindrical pin, such that the pin can engage within a groove of a bone fastener configured to penetrate the transverse bore of the intramedullary nail.

In the aspect described above, the second axis of the guiding structure may be oriented eccentrically with respect to the longitudinal axis of the proximal portion. Further, the through hole of the drive member may be arranged centrally. The drive member may be movably connected to the substantially cylindrical pin. The transverse bore of the proximal portion of the intramedullary nail may be formed as an angulated bore having a defined angle with respect to the longitudinal axis of the proximal portion.

The coupling unit may be configured to urge, upon moving of the coupling unit toward the distal portion of the intramedullary nail, the pin in the direction of the longitudinal axis of the proximal portion towards the distal portion, such that the pin can engage within the groove of the bone fastener to prevent rotation of the bone fastener about a longitudinal axis of the bone fastener.

In one implementation, the pin may define a longitudinal axis intersecting a longitudinal axis of the bone fastener. The pin may be formed as a bolt having a shaft and a tip with a ball-, circular-, cone-, flat-, U-, or V-shape. Further, the pin can be eccentrically arranged on the drive member.

The intramedullary nail may include a channel substantially along a longitudinal axis of the intramedullary nail. The channel of the nail may have a circular or angular shape in cross-section. A cannulation can be defined through the intramedullary nail by the channel of the intramedullary nail, the through hole of the drive member and the bore of the proximal portion of the intramedullary nail, such that a surgical wire may be inserted through the cannulation. The surgical wire may be a guide wire, a Kirschner-wire or any other kind of wire.

In one possible implementation, the drive member may have an external thread for threadable engagement with the intramedullary nail, e.g., with the proximal portion of the intramedullary nail. The drive member can further include a ring (made of, for example, synthetic material) arranged in a circumferential groove of the drive member. Alternatively, the ring may be arranged on the external thread of the drive member (e.g., in a groove of the external thread). The synthetic material of the ring may be deformable. Thus, the ring can be a deformable plastic ring. The proximal portion of the intramedullary nail may include an internal thread, wherein the external thread of the drive member can mate with the internal thread of the proximal portion. Further, the drive member may be formed as a short bolt.

The drive member may include a drive transmitting portion, and the pin may include a groove substantially arranged in a direction transverse to the longitudinal direction of the pin, wherein the drive transmitting portion can movably engage within the groove of the pin (e.g., such that rotation of the drive member may cause movement of the pin in the direction of the longitudinal axis of the proximal portion of the intramedullary nail). The drive transmitting portion may be rotatably supported in the groove of the pin.

In another implementation, the drive member may include a drive transmitting portion, and the pin may be arranged on a base member having a holding portion, wherein the drive transmitting portion can movably engage with the holding portion. Rotation of the drive member may cause movement of the pin in the direction of the longitudinal axis of the proximal portion of the intramedullary nail.

In the aspect described above, the base member may include a through hole for receiving a surgical wire. The base member may have a circular shape and the through hole may be oriented centrally or eccentrically. Further, the channel of the intramedullary nail, the bore of the proximal portion of the intramedullary nail, the through hole of the base member, the through hole of the drive member and a central bore of the proximal portion can define a cannulation, such that a surgical wire may be inserted through the cannulation.

The implant system may further comprise a retainer arranged in the proximal portion of the intramedullary nail, wherein the range of motion of the coupling unit in the proximal direction can be limited by the retainer. The retainer may be formed as a snap ring or spring ring having a defined spring constant. The retainer can further have a circular shape.

The bore of the proximal portion and the guiding structure may be arranged adjacent to each other, e.g., adjacent in transverse direction. The bore of the proximal portion of the intramedullary nail can be co-axially arranged. Further, the bore of the proximal portion of the intramedullary nail may be located at the medial side and the guiding structure of the proximal portion of the intramedullary nail may be located at the lateral side of the intramedullary nail. The bore of the proximal portion of the intramedullary nail and the guiding structure may thus be oriented eccentrically with respect to the longitudinal axis of the proximal portion of the intramedullary nail. Moreover, the guiding structure can be formed as a groove or a bore. The guiding structure may have a V-, U- or C-shape or the like in cross-section.

The implant system may comprise the bone fastener. The bone fastener can be formed as a lag screw or femoral neck screw or any kind of blade.

According to a further aspect, there is provided an intramedullary nail for use in orthopaedic surgery for fixation of a bone. The intramedullary nail comprises a proximal portion defining a longitudinal axis, a distal portion and a transverse bore. The proximal portion includes a bore defining a first axis and a guiding structure defining a second axis. The first axis and the second axis are substantially parallel to the longitudinal axis of the proximal portion of the intramedullary nail and are spaced apart from each other. The intramedullary nail further comprises a coupling unit captively held and movably arranged within the proximal portion of the intramedullary nail. The coupling unit includes a substantially cylindrical pin and a drive member with a through hole, wherein the guiding structure is configured to slidably receive the substantially cylindrical pin, such that the pin can engage within a groove of a bone fastener configured to penetrate the transverse bore of the intramedullary nail.

The coupling unit may be preassembled within the proximal portion of the intramedullary nail. Thus, the drive member and the substantially cylindrical pin may be preassembled within the proximal portion of the intramedullary nail. The drive member may be movably connected to the substantially cylindrical pin.

The intramedullary nail, the proximal portion thereof, the coupling unit, the substantially cylindrical pin, a base member thereof and/or the drive member may be configured as generally described above and hereinafter. The intramedullary nail may further have a cannulation, a retainer and/or a bone fastener, which may be configured as generally described above and hereinafter.

According to a further aspect there is provided a method of fracture fixation of bone, the method comprising the steps of inserting a guide wire into a marrow cavity of bone; inserting a cannulated intramedullary nail over the guide wire into the marrow cavity of bone, wherein the intramedullary nail comprises a proximal portion defining a longitudinal axis, a distal portion and a transverse bore, wherein the proximal portion includes a bore defining a first axis and a guiding structure defining a second axis, wherein the first axis and the second axis are substantially parallel to the longitudinal axis of the proximal portion of the intramedullary nail and are spaced apart from each other, and a coupling unit captively held and movably arranged within the proximal portion of the intramedullary nail, the coupling unit including a substantially cylindrical pin and a drive member with a through hole, wherein the guiding structure is configured to slidably receive the substantially cylindrical pin; removing the guide wire; inserting a bone fastener through the transverse bore of the intramedullary nail into bone for stabilization of the bone fracture; and driving the coupling unit for producing an engagement of the pin with the bone fastener penetrating the transverse bore of the intramedullary nail, thereby preventing rotation of the bone fastener.

Due to the fact that the bore and the guiding structure of the proximal portion of the intramedullary nail are spaced apart from each other, and the coupling unit, e.g., in form of a set screw, includes a substantially cylindrical pin and a drive member with a through hole, wherein the guiding structure slidably receives the cylindrical pin, the coupling unit (i.e., the pin and the drive member) can be preassembled or preloaded within the intramedullary nail, while allowing simultaneous passage of a surgical wire. In particular, the surgical procedure and the implantation of the intramedullary nail within an intramedullary canal of a femur is simplified and facilitated. Moreover, since the pin can engage with the bone fastener, any modifications of the current bone fastener design are not required.

BRIEF DESCRIPTION OF THE DRAWINGS

These and other features, aspects and advantages of the present disclosure will become more apparent from the following detailed description taken in conjunction with the accompanying drawings, wherein.

DETAILED DESCRIPTION

Figure 1:
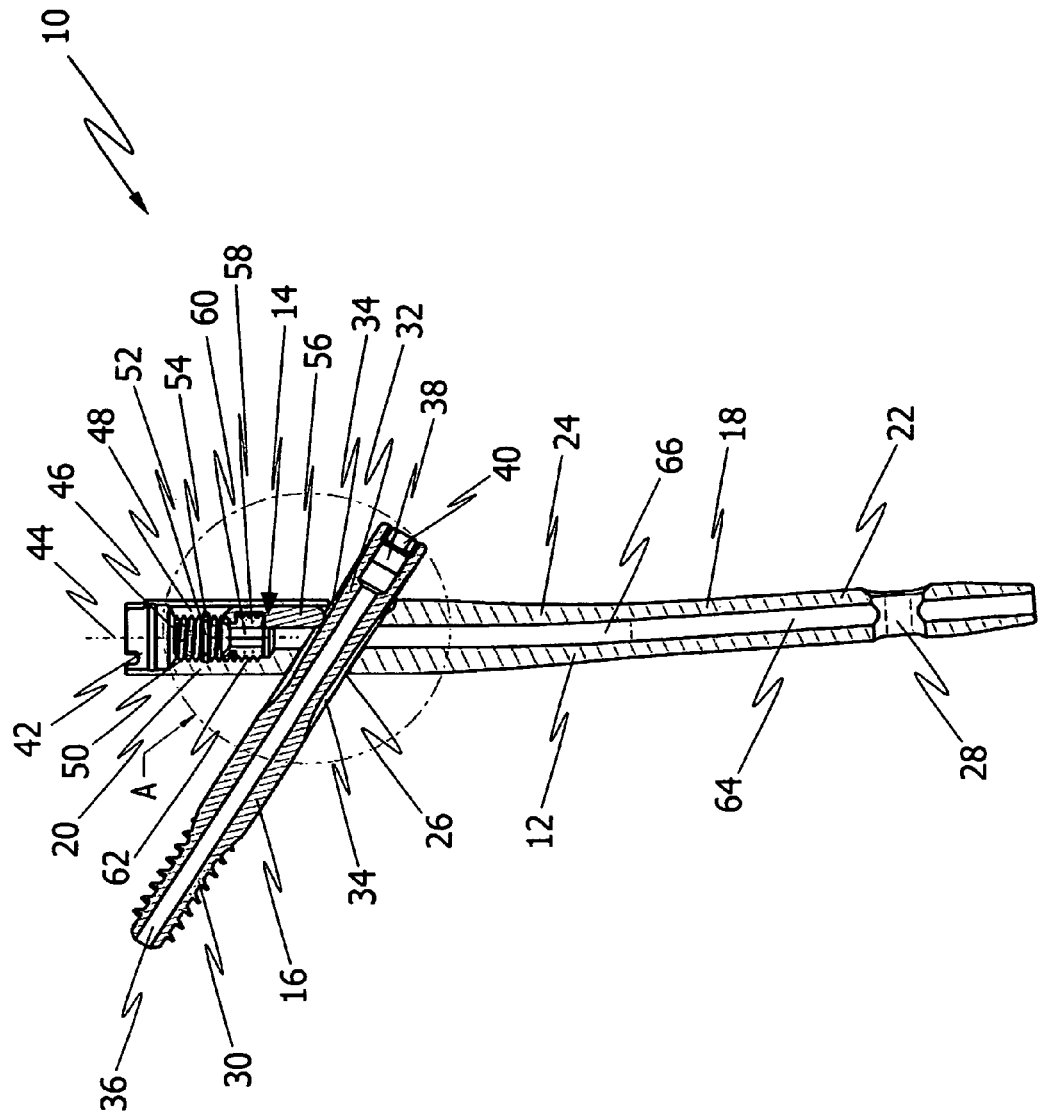
FIG. 1 is a cross-sectional view of an implant system embodiment.

Referring to FIG. 1, there is shown a cross-sectional view of an embodiment of an implant system 10 for use in orthopaedic surgery for fixation of bone, such as a femur (not shown in FIG. 1). The implant system 10 comprises an intramedullary nail 12, a coupling unit 14 and a bone fastener 16. The coupling unit 14 couples the bone fastener 16 to the intramedullary nail 12. The intramedullary nail 12 includes a rod-shaped body 18 insertable into the inner cavity (marrow cavity) of the femur, i.e., into the intramedullary canal of the femur. The rod-shaped body 18 of the intramedullary nail 12 includes a proximal portion 20, a distal portion 22 which is longer than the proximal portion 20, and a bent portion 24 located between the proximal portion 20 and the distal portion 22. In other words, the bent portion 24 connects the proximal portion 20 and the distal portion 22.

As shown in FIG. 1, the intramedullary nail 12 includes a transverse bore 26 located at the proximal portion 20. An axis of the transverse bore 26 has an angle with respect to a longitudinal axis of the intramedullary nail, such that the transverse bore 26 defines an angulated opening 26. The proximal portion 20 of the intramedullary nail 12 has a diameter sufficient to accommodate the transverse bore 26 therein, while the distal portion 22 of the intramedullary nail 12 has a smaller diameter with respect to the proximal portion 20, adapted to the shape of the marrow cavity of the femur in order to facilitate the insertion of the distal portion 22 into the intramedullary canal. Further, the distal portion 22 includes a through hole 28 extending orthogonal to the longitudinal axis of the intramedullary nail 12 at the distal portion 22. The through hole is formed at an end of the distal portion 22 of the intramedullary nail 12 for receiving a bone fastener, such as a locking screw in order to securely fix the intramedullary nail 12 to bone.

In the embodiment of the implant system 10 shown in FIG. 1, the bone fastener 16 is a femoral neck screw in the form of a lag screw 16. The lag screw 16 is adapted to penetrate the transverse bore 26 of the intramedullary nail 12. The lag screw has a front portion 30 including a thread, for example a coarse thread, and a rear portion 32. The rear portion 32 is provided with a plurality of longitudinally extending grooves 34 (two are shown in FIG. 1) arranged on the peripheral surface of the rear shaft portion 32 along the axis of the lag screw 16. Typically, four grooves 34 are disposed on the peripheral surface of the lag screw 16 at intervals of 90° around the longitudinal axis of the lag screw 16. Each groove 34 defines a ramp having a shallow end and a deeper end. The rising ramp extends from the shallow end at a rear end of the rear portion 32 towards the threaded front portion 30 to the deeper end. Further, the lag screw 16 includes a central cannulation 36 along the longitudinal axis of the lag screw 16. The rear portion 32 of the lag screw 16 includes at the rear end a co-axial bore 38 and a recess 40 (e.g., a hexalobular internal driving feature) for receiving a screw driver or a wrench (e.g., in the form of a entrainer driving feature).

As illustrated in FIG. 1, the proximal portion 20 of the intramedullary nail 12 includes a recess 42 for receiving an end cap or a tool, such as a holding instrument or targeting instrument (not shown in FIG. 1) at the upper end of the proximal portion 20. The proximal portion 20 defines a longitudinal axis 44 and further includes a bore 46 and a guiding structure 48. In the present embodiment, the bore 46 of the proximal portion 20 is co-axial with the longitudinal axis 44 of the proximal portion 20. As further shown in FIG. 1, the bore 46 includes an internal thread 50 and a recess portion 52 for receiving a retainer 54 in form of a snap ring.

The coupling unit 14 is preassembled and movably arranged within the proximal portion 20 of the intramedullary nail 12. The coupling unit 14 includes a substantially cylindrical pin 56 and a drive member 58 with a through hole 60. Thus, the coupling unit 14 is defined by the drive member 58 and the pin 56 connected thereto. Further, the drive member 58 is movably connected to the substantially cylindrical pin 56. The through hole 60 of the drive member 58 is a central through hole having an axis which coincides with the longitudinal axis 44 of the proximal portion 20. The drive member 58 further includes an external thread 62 for threadable engagement with the intramedullary nail 12, e.g., with the proximal portion 20 as shown in FIG. 1. The internal thread 50 of the proximal portion 20 mates with the external thread 62 of the drive member 58. In the present embodiment, the drive member 58 of the coupling unit 14 is movably arranged within the bore 46 of the proximal portion 20 of the intramedullary nail 12. Thus, the coupling unit 14 is captively held within the proximal portion 20 of the intramedullary nail 12. As also illustrated in FIG. 1, the guiding structure 48 slidably receives the substantially cylindrical pin 56 of the coupling unit 14, such that the pin 56 can engage within a groove 34 of the lag screw 16.

As further shown in FIG. 1, the intramedullary nail 12 includes a channel 64 substantially along the longitudinal axis of the intramedullary nail 12. Thus, a cannulation 66 is defined through the intramedullary nail 12 by the channel 64 of the intramedullary nail 12, the through hole 60 of the drive member and the bore 46 of the proximal portion 20, such that a surgical wire (not shown in FIG. 1) can be inserted through the cannulation 66.

Figure 2:
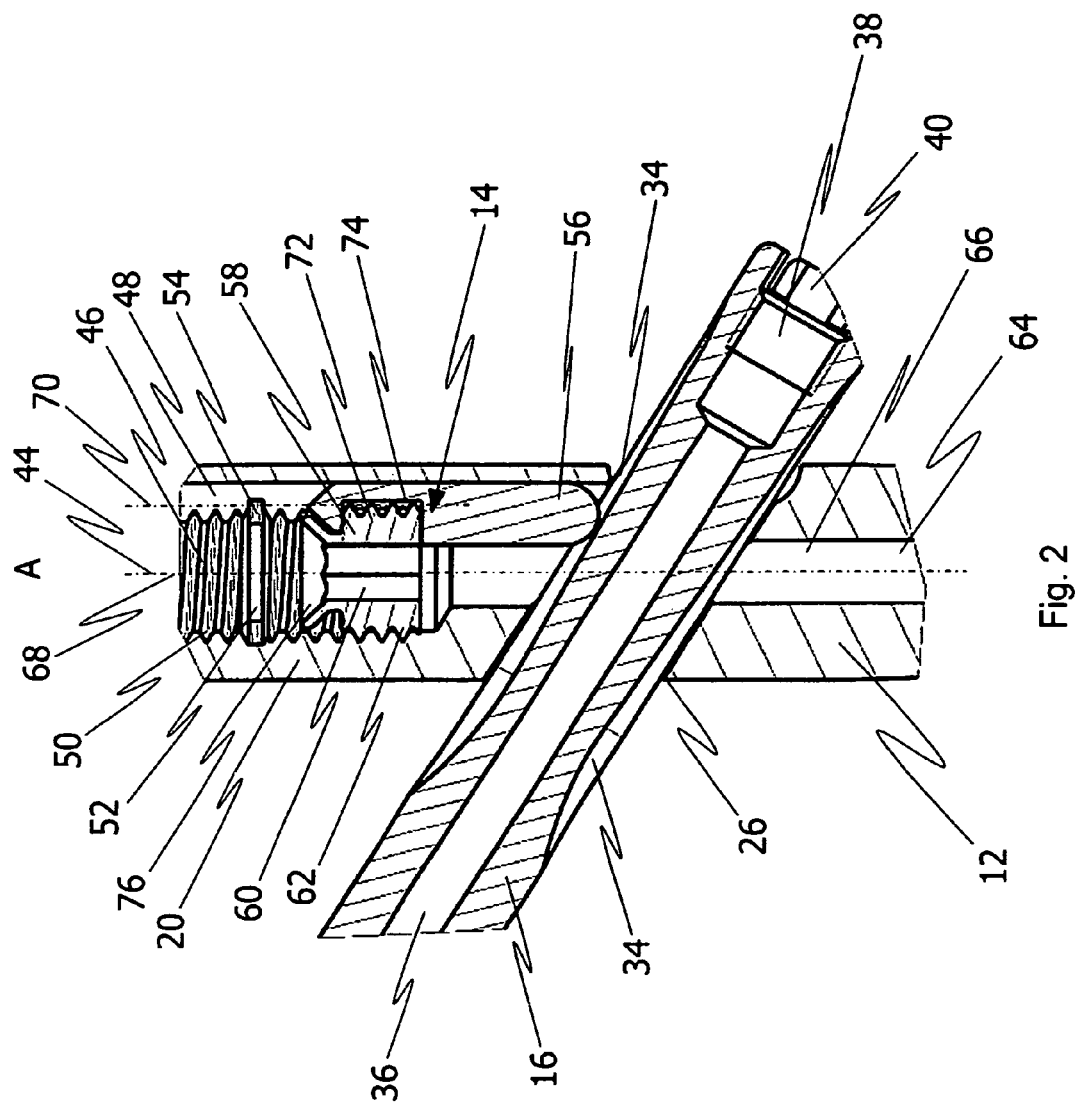
FIG. 2 is a detailed view of a proximal portion of the implant system embodiment shown in FIG. 1.

FIG. 2 illustrates a detailed view A of the proximal portion 20 of the intramedullary nail 12 shown in FIG. 1. As shown in FIG. 2, the bore 46 of the proximal portion 20 defines a first axis 68 which, in this case, coincides with the longitudinal axis 44 of the proximal portion 20. Further, the guiding structure 48 defines a second axis 70. The first axis 68 and the second axis 70 are substantially parallel to the longitudinal axis 44 of the proximal portion 20 of the intramedullary nail 12 and are spaced apart from each other. Moreover, the second axis 70 of the guiding structure 48 is oriented eccentrically with respect to the longitudinal axis 44 of the proximal portion 20. The bore 46 of the proximal portion and the guiding structure 48 are thus arranged adjacent to each other. In the present embodiment illustrated in FIGS. 1 and 2, the bore 46 of the proximal portion 20 is located centrally and the guiding structure 48 of the proximal portion 20 is located at the lateral side of the intramedullary nail 12. The bore 46 of the proximal portion 20 terminates at its lower end in the channel 64 of the intramedullary nail 12. The guiding structure 48 terminates at its lower end in the transverse bore of the proximal portion 20. In the present embodiment, the term "lower end" means that end which is nearer to the distal portion 22 of the intramedullary nail 12, and the term "upper end" is the opposite of the lower end. Further, the guiding structure 48 is formed as a groove having a circular shape (e.g., C-shape) in cross-section.

As also illustrated in FIG. 2, the pin 56 of the coupling unit 14 is eccentrically arranged on the drive member 58, i.e., arranged at an eccentric position (e.g., at a lateral position). Further, the pin 56 defines a longitudinal axis intersecting the longitudinal axis of the lag screw 16. The pin is formed as a bolt having a cylindrical shaft (here: a circular cylindrical) and a ball-shaped (i.e., circular shaped) tip at its lower end. The drive member 58 further includes a drive transmitting portion 72 for transmitting the movement of the drive member 58 to the pin 56. The pin includes a groove 74 at its upper end. The groove 74 of the pin 56 is substantially arranged in a direction transverse to the longitudinal direction of the pin 56. The drive transmitting portion 72 of the drive member 58 movably engages within the groove 74 of the pin 56. For this purpose, the drive transmitting portion 72 is rotatably supported in the groove 74 of the pin 56. Thus, rotation of the drive member 58 causes movement of the pin 56 in the direction of the longitudinal axis 44 of the proximal portion 20.

The drive member 58 of the coupling unit 14 has a receiving portion 76 in form of a cone having a recess (e.g., in the form of a hexalobular internal driving feature) for receiving a tool, screwdriver, wrench or the like. By driving the drive member 58 using such a tool, the entire coupling unit 14 moves along the longitudinal axis 44 of the proximal portion 20 of the intramedullary nail 12, since the external thread 62 of the drive member 58 mates with the internal thread 50 of the bore 46 of the proximal portion 20. In other words, the position of the coupling unit 14, and therewith the position of its pin 56, within the proximal portion 20 of the intramedullary nail 12 can be adjusted by screwing the drive member 54 of the coupling unit 14 along the longitudinal axis 44.

As shown in FIG. 2, the range of motion (i.e., the movement) of the coupling unit 14 in the proximal direction is limited by the retainer 54. The retainer 54 in form of a snap ring engages within the recess portion 52. The recess portion 52 is formed as a circumferential groove within the proximal portion of the intramedullary nail 12 to avoid an unintended disassembling of the coupling unit 14 and its drive member 58 and pin 56.

Upon moving of the coupling unit 14 towards the distal portion 22 of the intramedullary nail 12, the coupling unit 14 (particularly, the drive member 58 of the coupling unit 14) urges the pin 56 in the direction of the longitudinal axis 44 of the proximal portion 20 towards the distal portion 22 of the intramedullary nail 12. The pin 56 of the coupling unit 14 thus slides within the guiding structure 48 towards the lag screw 16. In a final position (as shown in FIG. 2), the pin 56 engages within a groove 34 of the lag screw 16 to prevent rotation of the lag screw 16 about its longitudinal axis.

As illustrated in FIGS. 1 and 2, the laterally arranged, eccentric pin 56 allows an engagement within a groove 34 of the lag screw 16. The medial cannulation 66 formed by the canal 64 of the intramedullary nail 12, the central through hole 60 of the drive member 58 and the bore 46 of the proximal portion 20 allows the simultaneous inserting of a guide wire.

During a surgical procedure, the intramedullary nail 12 is positioned and located in the intramedullary canal of a bone, e.g., the femur. Then, a hole is bored transversally through the femur, the neck of the femur and into the head thereof for receiving the lag screw 16. Then, the lag screw 16 is screwed into position through the transverse bore 26 of the intramedullary nail 12 by operating a tool, e.g, a screw driver, such that one of the longitudinal grooves 34 of the lag screw 16 is aligned in the uppermost position. The drive member 58 of the coupling unit 14, which is preassembled within the proximal portion 20 of the intramedullary nail 12, is then turned downwards (i.e., in the direction of the longitudinal axis 44 of the proximal portion 20 towards the distal portion 22 of the intramedullary nail 12) with a screw driver until the lower end of the pin 56 is engaged within one of the grooves 34 of the lag screw 16.

Provided that the coupling unit 14 is not completely tightened (i.e., the drive member 58 of the coupling unit 14 is not completely tightened), the lag screw 16 has the facility to slide within the transverse bore 26 only in a lateral direction (to the right in FIGS. 1 and 2) but is locked against rotation about its longitudinal axis. As the lag screw 16 is held against rotation by the coupling unit 14 (i.e., by the pin 56 of the coupling unit 14), it merely slides through the transverse bore 26 and draws the head of the femur into close engagement with the rest of the bone. Due to the rising ramp of the groove 34 of the lag screw 16, an uncontrolled medial sliding (to the left in FIGS. 1 and 2) of the lag screw 16 within the intramedullary nail 12 is prevented.

FIGS. 3 to 7 show another embodiment of a proximal portion with an alternative coupling unit embodiment, that can be adapted as needed (e.g., in terms of shape, length, width, thickness, etc.) for use in the intramedullary nail 12 of the implant system 10 shown in FIG. 1.

Figure 3:
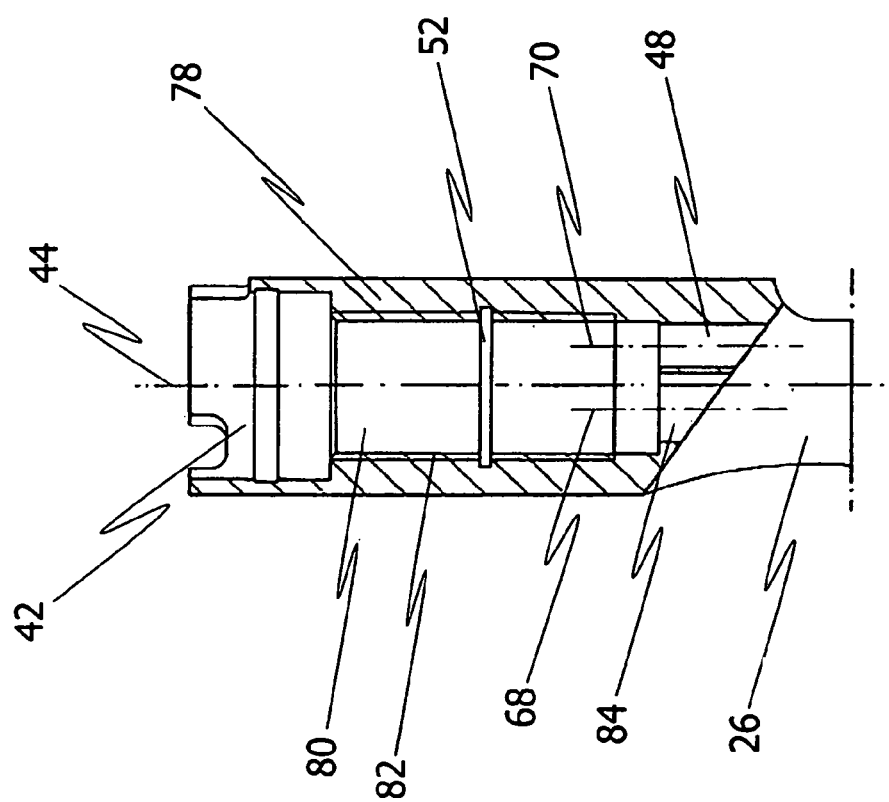
FIG. 3 is a cross-sectional view of an alternative embodiment of the proximal portion of an intramedullary nail.

FIG. 3 illustrates a cross-sectional view of the alternative embodiment of the proximal portion 78 of the intramedullary nail. The proximal portion 78 includes a central bore 80 having an internal thread 82. The proximal portion 78 further includes the recess portion 52 in form of the groove 52 for receiving the retainer 54 within the central bore 80. Moreover, the proximal portion 78 also includes the recess 42 for receiving an end cap or a tool, such as a holding instrument or targeting instrument (not shown in FIG. 3) at the upper end of the proximal portion 78.

As shown in FIG. 3, the guiding structure 48 is formed as a bore 48 located at the lateral side (right side in FIG. 3) of the intramedullary nail. The guiding structure 48 terminates at its upper end in the central bore 80 of the proximal portion 78 and at its lower end in the transverse bore 26. Also in this present embodiment, the term "lower end" means that end which is nearer to the distal portion of the intramedullary nail, and the term "upper end" is the opposite of the lower end. As further illustrated in FIG. 3, the proximal portion 78 includes a bore 84 which is arranged adjacent to the guiding structure 48. The bore 84 of the proximal portion 78 also terminates at its upper end in the central bore 80 and at its lower end in the transverse bore 26 of the intramedullary nail. Further, the bore 84 defines the first axis 68 and the guiding structure 48 defines the second axis 70, wherein the first axis 68 and the second axis 70 are substantially parallel to the longitudinal axis 44 of the proximal portion 78 and are spaced apart from each other (here: spaced apart from each other in the transverse direction), as shown in FIG. 3.

Figure 4:
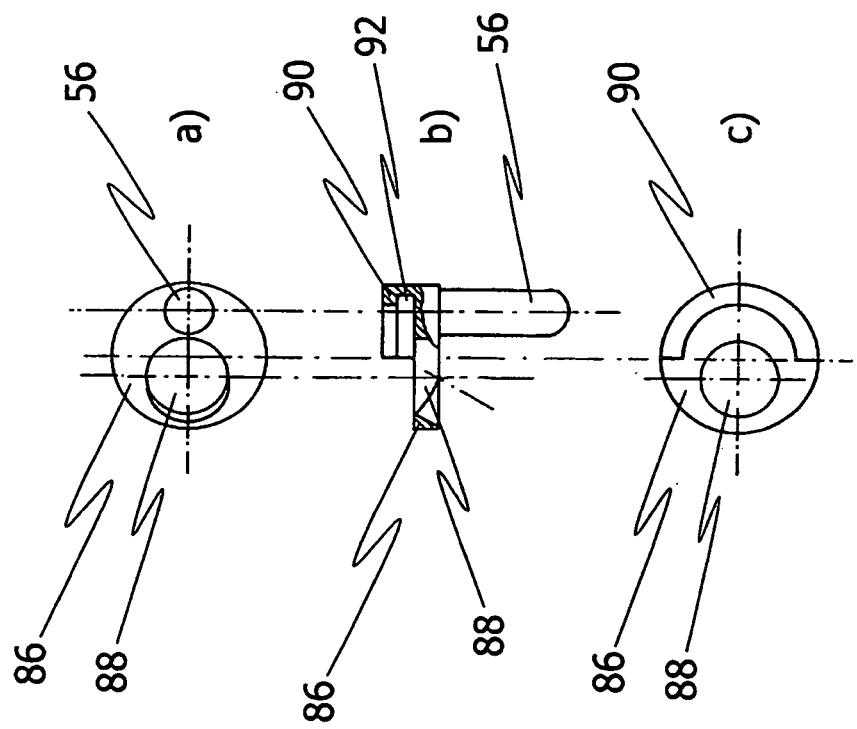
FIG. 4 shows top, side and bottom views of an alternative pin embodiment.

FIG. 4 illustrates a bottom view a), a side view b), and a top view c) of an alternative pin embodiment having a base member 86 in the form of a plate 86 on which the pin 56 is arranged. In the present embodiment, the pin 56 is integral (i.e., integrally formed) with the plate 86. The pin is configured as generally described above with respect to FIGS. 1 and 2. The plate 86 has a circular shape and a through hole 88 for receiving a surgical wire or a guiding wire. The pin 56 and the through hole 88 are eccentrically arranged on the plate 86.

The plate 86 further has a holding portion 90. The holding portion 90 is arranged on the upper surface opposite to the lower surface on which the pin 56 is arranged. The holding portion 90 extends from the plate 86 and has a L-shape in cross-section as shown in the side view b) of FIG. 4. Further, the holding portion 90 forms an arc along the outer peripheral side of the plate 86 as illustrated in the top view c) of FIG. 4. For this purpose, the arc formed by the holding portion 90 may extend over 180° or less. Thus, the plate 86 and the holding portion 90 thereof form a circular groove 92 for receiving a part of a drive member as described hereinafter.

Figure 5:
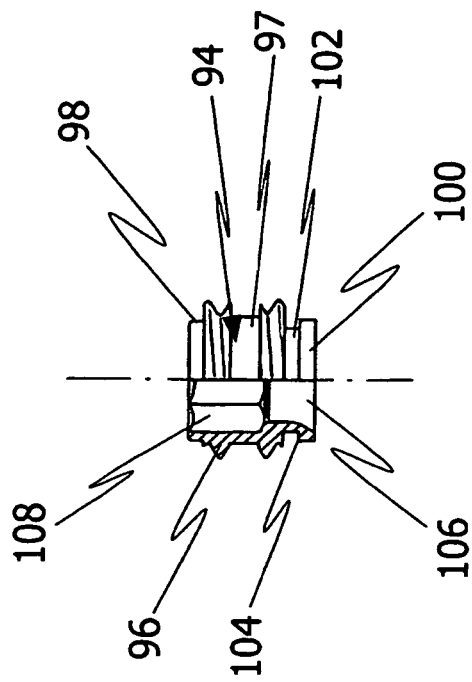
FIG. 5 is a side view of an alternative drive member embodiment.

Referring to FIG. 5, there is shown a side view of another embodiment of a drive member 94 in form of a short bolt. The drive member 94 has an external thread 96 on its outer peripheral surface 98. The external thread 96 of the drive member is interrupted by a circumferential groove 97. The circumferential groove 97 may receive a ring (not shown in FIG. 5) made of synthetic material. The drive member 94 further includes a drive transmitting portion 100. The drive transmitting portion 100 is formed as a flange arranged on the drive member 94, wherein the diameter of the drive transmitting portion 100 is slightly greater than the diameter of a shaft portion 102 of the drive member 94. Thus, a circumferential step 104 is defined by the drive transmitting portion 100 and the shaft portion 102 of the drive member 94. The drive transmitting portion 100 can movably engage with the holding portion 90 of the plate 86, wherein the step 104 of the drive member 94 engages within the circular groove 92 of the holding portion 90. The drive member 94 further comprises a central through hole 106 for receiving a guide wire and a recess 108 (e.g., in the form of a hexalobular internal driving feature or internal hexagon) for receiving a tool, such as a screwdriver, a wrench, or the like.

Figure 6:
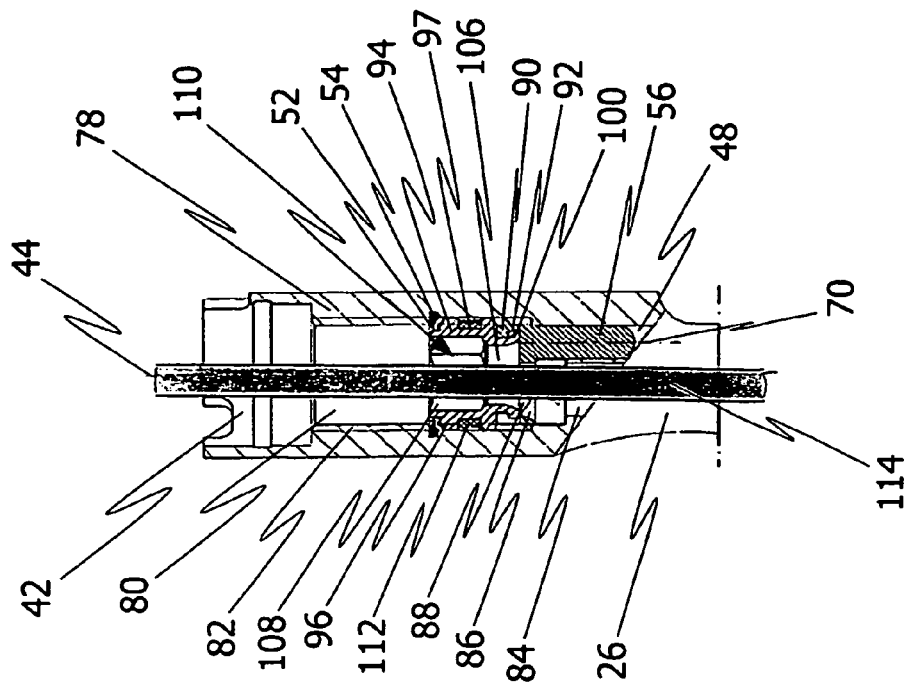
FIG. 6 is a cross-sectional view of the alternative embodiment of the proximal portion shown in FIG. 3 including the pin embodiment shown in FIG. 4 and the drive member embodiment shown in FIG. 5.
Figure 7:
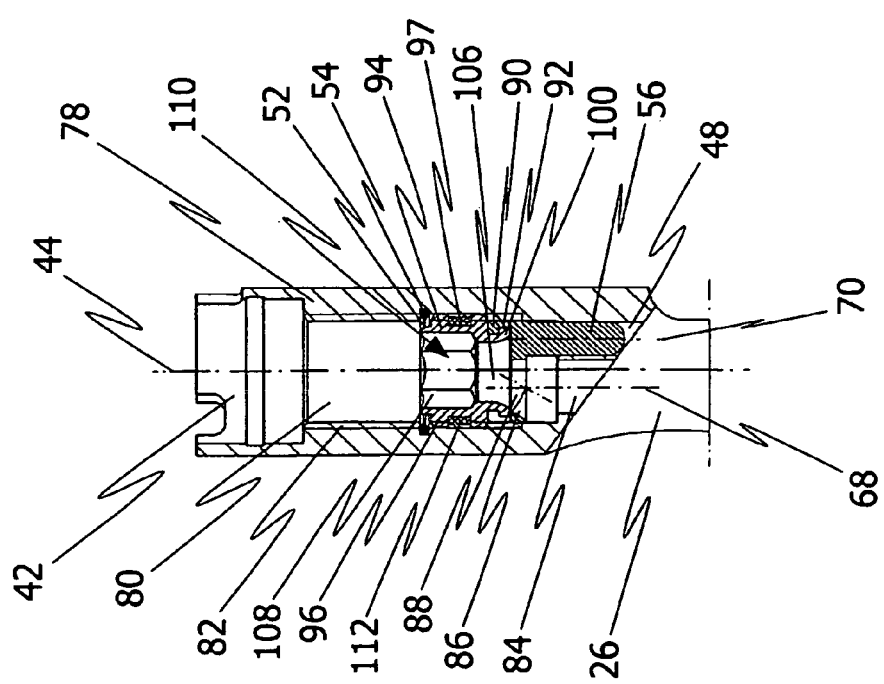
FIG. 7 is a cross-sectional view of the assembling shown in FIG. 6 including a guide wire.

As illustrated in FIGS. 6 and 7, a coupling unit 110 is formed by the drive member 94 and the plate 86 having the pin 56, wherein the drive member 94 is movably connected to the plate 86 as described above. Further, the coupling unit 110, i.e, the drive member 94 and the plate 86 with the pin 56, is preassembled within the proximal portion 78 of the intramedullary nail. The guiding structure 48 of the proximal portion 78 of the intramedullary nail has a diameter which is slightly larger than the diameter of the pin 56, such that an optimal guiding and sliding respectively of the pin 56 within the bore 48 is guaranteed. As shown in FIG. 6, the pin 56 of the coupling unit 110 is located within the guiding structure 48 in the preassembled configuration. Moreover, the external thread 96 of the drive member 94 of the coupling unit 110 mates with the internal thread 82 of the central bore 80 of the proximal portion 78 of the intramedullary nail, such that the entire coupling unit 110 is captively held and movably arranged within the proximal portion 78 of the intramedullary nail. Thus, the height adjustment of the coupling unit 110, and therewith of the pin 56, is driven by the drive member 94, as generally described above with respect to FIGS. 1 and 2 and hereinafter. To avoid an unintended loosening of the coupling unit 110, the driving member of the coupling unit 110 has a ring 112 made of synthetic material arranged in the circumferential groove 97 of the drive member 94 as shown in FIGS. 6 and 7. Furthermore, the retainer 54 is positioned and engaged into the recess portion 52 formed as groove 52 within the central bore 80 of the proximal portion 78 of the intramedullary nail to avoid an unintended disassembling of the coupling unit 110 or of its parts (drive member 94 and plate 86 with pin 56). Thus, the retainer 54 functions as a limiter which limits the range of motion of the coupling unit 110 in the proximal direction.

As shown in FIGS. 6 and 7, the drive transmitting portion 100 of the drive member 94 engages on the holding portion 90 of the plate 86. The plate 86 is centrally inserted within the proximal portion 78 of the intramedullary nail, providing rotational stability of the pin 56 of the coupling unit 110. Thus, rotation of the drive member 94 of the coupling unit 110 causes movement of the pin 56, which is slidably received in the guiding structure 48, in the direction of the longitudinal axis of the proximal portion 78 of the intramedullary nail. The rotation of the drive member 94 is performed by a tool such as a screw driver or the like which engages within the recess 108 of the drive member 94. Upon moving of the coupling unit 110 along the longitudinal axis 44 of the proximal portion 78 of the intramedullary nail, the coupling unit 110 (particularly, the drive member 94 of the coupling unit 110) urges the pin 56 through the guiding structure 48 in the direction of the longitudinal axis 44 towards the distal portion of the intramedullary nail, such that the pin 56 engages within a groove of the lag screw to prevent rotation of the lag screw about its longitudinal axis.

As further illustrated in FIGS. 6 and 7, the channel of the intramedullary nail, the bore 84 of the proximal portion 78 of the intramedullary nail, the through hole 88 of the plate 86, the through hole 106 of the drive member 94, and the central bore 80 of the proximal portion 78 define a cannulation. A guide wire 114 may be inserted through the cannulation as shown in FIG. 7.

In an exemplary method for fracture fixation of bone, the guide wire 114 is firstly inserted into a marrow cavity of bone. Then, the cannulated intramedullary nail 12 is inserted over the guide wire 114 into the marrow cavity of bone. The intramedullary nail 12 comprises the proximal portion 20 or 78, the transverse bore 26 and the coupling unit 14 or 110 as generally described above. The guide wire 114 is then removed and a bone fastener 16 is inserted through the transverse bore 26 of the intramedullary nail 12 into bone for stabilization of the bone fracture. Finally, the coupling unit of the intramedullary nail 12 is driven for producing an engagement of the pin 56 with the bone fastener 16 penetrating the transverse bore 26 of the intramedullary nail 12, thereby preventing rotation of the bone fastener 16.

Since the proximal portion of the intramedullary nail and the coupling unit having the drive member and the pin are configured as described above, the coupling unit can be preassembled or preloaded within the intramedullary nail, while allowing a simultaneous inserting/passage of a guide wire. The channel of the intramedullary nail, the bore(s) of the proximal portion of the intramedullary nail and the through hole(s) of the coupling unit (which together define a cannulation) may be substantially aligned to permit insertion of a guide wire completely through the preassembled unit and the intramedullary nail. Thus, a guide wire can be used to guide the intramedullary nail, including the preassembled coupling unit, into the intramedullary canal of, e.g., the femur. Therefore, the coupling unit has not to be assembled intraoperatively. Consequently, the operation steps that need to be performed by a surgeon are reduced, whereby the surgical procedure and the implantation of the intramedullary nail within an intramedullary canal of a femur is facilitated and simplified. Due to this fact, the operation time is reduced. Since the intramedullary nail is provided with the coupling unit (including the pin and the drive member movably connected thereto) that is preassembled into the hollow portion (bore) of the proximal portion of the intramedullary nail, the amount of time associated with implanting the intramedullary nail as well as the number of parts which have to be handled by a surgeon is reduced.

All parts of the implant system described above are easily and cheaply produceable with the current state of machine tools. Moreover, since the pin can engage within a groove of the bone fastener, any modifications or changes of the current bone fasteners are not necessary. Since the guide wires deviate to an eccentric position (e.g., to the medial side) within the intramedullary nail due to the bending of the intramedullary nail, the eccentric arrangement of the pin of the coupling unit and in particular of the bore of the proximal portion of the intramedullary nail facilitates the fence of the guide wire inside the intramedullary nail.

While the rod-shaped body of the intramedullary nail includes a distal portion and a bent portion in the embodiment illustrated in the drawings, the nail body can be adapted as needed (e.g., in terms of shape, length, width, thickness, etc.) for use in orthopaedic surgery for fixation of bone and for insertion into an intramedullary canal of, e.g., a femur. Thus, the intramedullary nail can be adapted to different applications and may thus have a different shape. Moreover, while the threads as shown herein are one start threads, they could also be multiple start threads (e.g., a two-start thread).

While the bone fastener as described herein is formed as a lag screw, the bone fastener can be of any type of, e.g., a femoral neck screw or any kind of blade, and can be adapted to different applications as needed. The bone fasteners may thus have different diameters, lengths, shapes or threads. Further, the bone fastener and the implant described above can generally be made of stainless steel, titanium or any other biocompatible material.

While the above embodiments have exemplarily been described in relation to a bone screw and an intramedullary nail, it will be readily apparent that the techniques presented herein can also be implemented in combination with other types of bone fasteners (such as bone pegs having a rod-like or pin-like shafts, wire-like bone fasteners such as Kirschner wires, etc.) as well as other types of implants (such as bone plates, bone distractors, etc). Accordingly, the present disclosure is not limited to any type of bone fastener or any type of implant.

The features described in the above description taken in conjunction with the accompanying drawings can be readily combined to result in different embodiments. It will thus be apparent that the disclosure described above may be varied in many ways. Such variations are not to be regarded as a departure from the scope of the invention, and all modifications are intended to be included within the scope of the following claims.

The invention claimed is:

1. An implant system for use in orthopaedic surgery for fixation of bone, comprising:
    an intramedullary nail with a proximal portion defining a central longitudinal axis, a distal portion and a transverse bore with a central longitudinal axis at an angle with respect to the central longitudinal axis of the proximal portion, wherein the proximal portion includes a bore defining a bore central axis and a guiding structure in a wall surrounding the proximal portion bore, the guiding structure having a central longitudinal axis, wherein the proximal portion bore central axis and the central longitudinal axis of the guiding structure are substantially parallel to the central longitudinal axis of the proximal portion of the intramedullary nail and are spaced apart from each other;
    a coupling unit adapted to be movably arranged within the proximal portion of the intramedullary nail, the coupling unit including a substantially cylindrical pin and a drive member with a through hole;
    wherein the guiding structure is at least part-cylindrical and concave and configured to slidably receive the substantially cylindrical pin, such that the substantially cylindrical pin can engage within a groove of a bone fastener configured to penetrate said transverse bore of the intramedullary nail, with the substantially cylindrical pin having a central longitudinal axis intersecting the central longitudinal axis of said transverse bore and thereby a central longitudinal axis of the bone fastener when the bone fastener penetrates the transverse bore of the intramedullary nail; and
    wherein the drive member includes a drive transmitting portion, and the substantially cylindrical pin includes a groove substantially arranged in a direction transverse to the direction of the central longitudinal axis of the substantially cylindrical pin, wherein the drive transmitting portion is rotatably supported in the groove of the substantially cylindrical pin.

2. The implant system according to claim 1, wherein the coupling unit is configured to urge, upon moving of the coupling unit toward the distal portion of the intramedullary nail, the substantially cylindrical pin in a direction parallel to the central longitudinal axis of the proximal portion towards the distal portion, such that the substantially cylindrical pin engages within the groove of the bone fastener to prevent rotation of the bone fastener about the central longitudinal axis of the bone fastener.

3. The implant system according to claim 1, wherein the guiding structure of the proximal portion is located at a lateral side of the intramedullary nail.

4. The implant system according to claim 1, wherein there is only a single substantially cylindrical pin slidably mounted in the guiding structure and wherein the guiding structure is a channel open to the bore, the channel having a central longitudinal axis lying in a plane containing the central longitudinal axis of the transverse bore.

5. The implant system according to claim 1, wherein the intramedullary nail includes a channel substantially along a longitudinal axis of the intramedullary nail.

6. The implant system according to claim 5, wherein a cannulation is defined through the intramedullary nail by the channel of the intramedullary nail, the through hole of the drive member and the bore of the proximal portion, such that a surgical wire may be inserted through the cannulation.

7. The implant system according to claim 5, wherein the substantially cylindrical pin is arranged on a base member and wherein the channel of the intramedullary nail, the bore of the proximal portion, a through hole in the base member and the through hole of the drive member define a cannulation, such that a surgical wire may be inserted through the cannulation.

8. The implant system according to claim 1, wherein the drive member has an external thread for threadable engagement with the intramedullary nail.

9. The implant system according to claim 8, wherein the proximal portion of the intramedullary nail includes an internal thread, wherein the external thread of the drive member mates with the internal thread of the proximal portion.

10. The implant system according to claim 1, wherein the drive member further includes a ring arranged in a circumferential groove of the drive member.

11. The implant system according to claim 1, further comprising a retainer arranged in the proximal portion of the intramedullary nail, wherein the range of motion of the coupling unit in the proximal direction is limited by the retainer.

12. The implant system according to claim 1, wherein the bore of the proximal portion and the guiding structure are arranged adjacent to each other.

13. The implant system according to claim 1, wherein the bore of the proximal portion is located at a medial side and the guiding structure of the proximal portion is located at a lateral side of the intramedullary nail.

14. The implant system according to claim 1, wherein the guiding structure is formed as a groove or a partially open bore.

15. The implant system according to claim 1, further comprising the bone fastener.

16. An implant system for use in orthopaedic surgery for fixation of bone, comprising:

an intramedullary nail with a proximal portion defining a central longitudinal axis, a distal portion and a transverse bore with a central longitudinal axis at an angle with respect to the central longitudinal axis of the proximal portion, wherein the proximal portion includes a bore defining a bore central axis and a guiding structure in a wall surrounding the proximal portion bore the guiding structure having a central longitudinal axis, wherein the proximal portion bore central axis and the central longitudinal axis of the guiding structure are substantially parallel to the central longitudinal axis of the proximal portion of the intramedullary nail and are spaced apart from each other;

a coupling unit adapted to be movably arranged within the proximal portion of the intramedullary nail, the coupling unit including a substantially cylindrical pin and a drive member with a through hole;

wherein the guiding structure is part-cylindrical and concave and configured to slidably receive the substantially cylindrical pin, such that the substantially cylindrical pin can engage within a groove of a bone fastener configured to penetrate said transverse bore of the intramedullary nail, with the substantially cylindrical pin having a central longitudinal axis intersecting the central longitudinal axis of said transverse bore and thereby a central longitudinal axis of the bone fastener when the bone fastener penetrates the transverse bore of the intramedullary nail; and wherein the drive member includes a drive transmitting portion, and the substantially cylindrical pin includes a groove substantially arranged in a direction transverse to the direction of the central longitudinal axis of the substantially cylindrical pin, wherein the drive transmitting portion movably engages within the groove of the substantially cylindrical pin.

17. The implant system according to claim 16, wherein the coupling unit is configured to urge, upon moving of the coupling unit toward the distal portion of the intramedullary nail, the substantially cylindrical pin in a direction parallel to the central longitudinal axis of the proximal portion towards the distal portion, such that the substantially cylindrical pin engages within the groove of the bone fastener to prevent rotation of the bone fastener about the central longitudinal axis of the bone fastener.

18. The implant system according to claim 16, wherein the guiding structure of the proximal portion is located at a lateral side of the intramedullary nail.

19. The implant system according to claim 16, wherein there is only a single substantially cylindrical pin slidably mounted in the guiding structure and wherein the guiding structure is a channel open to the bore, the channel having a central longitudinal axis lying in a plane containing the central longitudinal axis of the transverse bore.

20. The implant system according to claim 16, wherein the intramedullary nail includes a channel substantially along a longitudinal axis of the intramedullary nail.

21. The implant system according to claim 16, wherein the drive member has an external thread for threadable engagement with the intramedullary nail.

22. The implant system according to claim 21, wherein the proximal portion of the intramedullary nail includes an internal thread, wherein the external thread of the drive member mates with the internal thread of the proximal portion.

23. The implant system according to claim 16, wherein the drive member further includes a ring arranged in a circumferential groove of the drive member.

24. The implant system according to claim 16, wherein the bore of the proximal portion is located at a medial side and the guiding structure of the proximal portion is located at a lateral side of the intramedullary nail.

25. The implant system according to claim 16, wherein the guiding structure is formed as a groove or a partially open bore.

26. An intramedullary nail for use in orthopaedic surgery for fixation of bone, comprising:
a proximal portion defining a central longitudinal axis, a distal portion and a transverse bore with a central longitudinal axis at an angle with respect to the central longitudinal axis of the proximal portion, wherein the proximal portion includes a longitudinal bore defining a bore central axis and a guiding structure defining a central longitudinal axis, wherein the longitudinal bore central axis and the guiding structure central longitudinal axis are substantially parallel to the central longitudinal axis of the proximal portion of the intramedullary nail and are spaced apart from each other;
a coupling unit captively held and movably arranged within the proximal portion of the intramedullary nail, the coupling unit including a substantially cylindrical pin and a drive member with a through hole;
wherein the guiding structure is configured to slidably receive the substantially cylindrical pin, such that the pin can engage within a groove of a bone fastener configured to penetrate said transverse bore of the intramedullary nail, wherein the pin has a longitudinal central axis intersecting the central longitudinal axis of said transverse bore and a central longitudinal axis of the bone fastener; and
wherein the drive member includes a drive transmitting portion, and the substantially cylindrical pin includes a groove substantially arranged in a direction transverse to a longitudinal direction of the substantially cylindrical pin, wherein the drive transmitting portion movably engages within the groove of the substantially cylindrical pin.

27. The intramedullary nail according to claim 26, wherein the coupling unit is preassembled within the proximal portion of the intramedullary nail.

28. The intramedullary nail according to claim 26, wherein the central longitudinal axis of the guiding structure is oriented eccentrically with respect to the central longitudinal axis of the proximal portion.

29. The intramedullary nail according to claim 26, wherein the coupling unit is configured to urge, upon moving of the coupling unit toward the distal portion of the intramedullary nail, the substantially cylindrical pin in a direction of the central longitudinal axis of the proximal portion towards the distal portion, such that the substantially cylindrical pin engages within the groove of the bone fastener to prevent rotation of the bone fastener about the central longitudinal axis of the bone fastener.

30. The intramedullary nail according to claim 26, wherein there is only a single cylindrical pin slidably mounted in the guiding structure and wherein the guiding structure is a channel open to the bore, the channel having a central longitudinal axis lying in a plane containing the central longitudinal axis of the transverse bore.

31. The intramedullary nail according to claim 26, wherein the intramedullary nail includes a channel substantially along a longitudinal axis of the intramedullary nail.

32. The intramedullary nail according to claim 31, wherein a cannulation is defined through the intramedullary nail by the channel of the intramedullary nail, the through hole of the drive member and the longitudinal bore of the proximal portion, such that a surgical wire may be inserted through the cannulation.

33. The intramedullary nail according to claim 31, wherein the substantially cylindrical pin is arranged on a base member and wherein the channel of the intramedullary nail, the longitudinal bore of the proximal portion, a through hole in the base member and the through hole of the drive member define a cannulation, such that a surgical wire may be inserted through the cannulation.

34. The intramedullary nail according to claim 26, wherein the drive member has an external thread for threadable engagement with the intramedullary nail.

35. The intramedullary nail according to claim 34, wherein the proximal portion of the intramedullary nail includes an internal thread, wherein the external thread of the drive member mates with the internal thread of the proximal portion.

36. The intramedullary nail according to claim 26, wherein the drive member includes a drive transmitting portion, and the pin is arranged on a base member having a holding portion, wherein the drive transmitting portion movably engages with the holding portion.

37. The intramedullary nail according to claim 36, wherein the base member includes a through hole for receiving a surgical wire.

38. The intramedullary nail according to claim 26, further comprising a retainer arranged in the proximal portion of the intramedullary nail, wherein the range of motion of the coupling unit in the proximal direction is limited by the retainer.

39. The intramedullary nail according to claim 26, wherein the central longitudinal axes of the bore of the proximal portion and the guiding structure are arranged adjacent to each other.

40. The intramedullary nail according to claim 26, wherein the longitudinal bore of the proximal portion is located at a medial side and the guiding structure of the proximal portion is located at a lateral side of the intramedullary nail.

41. The intramedullary nail according to claim 26, wherein the longitudinal bore of the proximal portion is located centrally and the guiding structure of the proximal portion is located at a lateral side of the intramedullary nail.

42. The intramedullary nail according to claim 26, wherein the guiding structure is formed as a closed bore or a partially open bore.

43. An implant system for use in orthopaedic surgery for fixation of bone, comprising:
a bone fastener having a groove formed on an outer surface thereof;
an intramedullary nail with a proximal portion defining a central longitudinal axis, a distal portion and a transverse bore with a central longitudinal axis at an angle with respect to the central longitudinal axis of the proximal portion for receiving the bone fastener, wherein the proximal portion includes a bore defining a bore central axis and a guiding structure in a wall surrounding the proximal portion bore, the guiding structure having a central longitudinal axis, wherein the proximal portion bore central axis and the central longitudinal axis of the guiding structure are substantially parallel to the central longitudinal axis of the proximal portion of the intramedullary nail and are spaced apart from each other;

a coupling unit adapted to be movably arranged within the proximal portion of the intramedullary nail, the coupling unit including a substantially cylindrical pin and a drive member with a through hole;

wherein the guiding structure is at least part-cylindrical and concave and configured to slidably receive the substantially cylindrical pin, such that the substantially cylindrical pin can slide axially in the guiding structure in the direction of the guiding structure central longitudinal axis into engagement with the groove of the bone fastener configured to penetrate the transverse bore of the intramedullary nail, with the substantially cylindrical pin having a central longitudinal axis intersecting the central longitudinal axis of said transverse bore and thereby a central longitudinal axis of the bone fastener when the bone fastener penetrates the transverse bore of the intramedullary nail; and wherein the drive member includes a drive transmitting portion, and the substantially cylindrical pin includes a groove substantially arranged in a direction transverse to the direction of the central longitudinal axis of the substantially cylindrical pin, wherein the drive transmitting portion is rotatably supported in the groove of the substantially cylindrical pin.

\* \* \* \* \*